United States Patent
Lien

(10) Patent No.: US 10,688,103 B2
(45) Date of Patent: Jun. 23, 2020

(54) METHODS FOR TREATING HYPERSOMNIA

(71) Applicant: BALANCE THERAPEUTICS, INC., San Bruno, CA (US)

(72) Inventor: Lyndon Lien, Hillsborough, CA (US)

(73) Assignee: BALANCE THERAPEUTICS, INC., Burlingame, CA (US)

( * ) Notice: Subject to any disclaimer, the term of this patent is extended or adjusted under 35 U.S.C. 154(b) by 56 days.

(21) Appl. No.: 15/303,725

(22) PCT Filed: Apr. 14, 2015

(86) PCT No.: PCT/US2015/025696
§ 371 (c)(1),
(2) Date: Oct. 12, 2016

(87) PCT Pub. No.: WO2015/160766
PCT Pub. Date: Oct. 22, 2015

(65) Prior Publication Data
US 2018/0169107 A1  Jun. 21, 2018

Related U.S. Application Data

(60) Provisional application No. 61/979,918, filed on Apr. 15, 2014.

(51) Int. Cl.
*A61K 31/55* (2006.01)
*A61P 25/00* (2006.01)
*A61K 9/00* (2006.01)
*C07D 487/04* (2006.01)

(52) U.S. Cl.
CPC .......... *A61K 31/55* (2013.01); *A61K 9/0053* (2013.01); *A61P 25/00* (2018.01); *C07D 487/04* (2013.01)

(58) Field of Classification Search
None
See application file for complete search history.

(56) References Cited

U.S. PATENT DOCUMENTS

| | | | |
|---|---|---|---|
| 8,729,067 B2 | 5/2014 | Garner et al. | |
| 8,946,206 B2 | 2/2015 | Garner et al. | |
| 9,453,020 B2 | 9/2016 | Lien | |
| 2009/0325999 A1* | 12/2009 | Du | A61K 31/135 514/299 |
| 2011/0028418 A1* | 2/2011 | Parker | A61K 31/5517 514/29 |
| 2011/0038850 A1 | 2/2011 | Bagnol et al. | |
| 2012/0157445 A1* | 6/2012 | Garner | A61K 36/16 514/214.02 |

FOREIGN PATENT DOCUMENTS

| | | |
|---|---|---|
| JP | 2006137746 A | 6/2006 |
| WO | 2007/139818 A2 | 12/2007 |
| WO | 2008085888 A1 | 7/2008 |
| WO | 2012/114342 A1 | 8/2012 |
| WO | 2012/151343 A1 | 11/2012 |

OTHER PUBLICATIONS

Gelfuso et al., Neurosci. Lett., 543, 2013, 12-16 (Year: 2013).*
Rye et al., 2012, Sci. Tansl. Med. 4, 161ra151, pp. 1-10 (Year: 2012).*
Kelty et al., Journal of Psychopharmacology 2014, vol. 28(7) 703-706 (Year: 2014).*
MacDonald et al., Nature vol. 267 Jun. 23, 1977 pp. 720-721 (Year: 1977).*
Database Caplus Chemical Abstracts Service, Columbus, Ohio, US; Database Accession No. 1992:73028, Abstract of Simmonds et al., European Journal of Pharmacology (1982), 80(4), 347-58 (Year: 1982).*
Ali et al., "Idiopathic hypersomnia: clinical features and response to treatment", J Clin Sleep Med., 5(6):562-568 (2009).
Gelfuso et al., "Parawixin2, a novel non-selective GABA uptake inhibitor from Parawixia bistriata spider venom, inhibits pentylenetetrazole-induced chemical kindling in rats", Neurosci Lett., 543:12-6 (2013).
Harris et al., "Hypersomnias of central origin", Neurol Clin., 30(4)1027-1044 (2012).
Kanbayashi et al., "CSF histamine contents in narcolepsy, idiopathic hypersomnia and obstructive sleep apnea syndrome", Sleep, 32(2):181-187 (2009).
Kelty et al., "Use of subcutaneous flumazenil preparations for the treatment of idiopathic hypersomnia: A case report", J Psychopharmacol. 28(7):703-706 (2014).
Montplaisir et al., "Narcolepsy and idiopthic hypersomnia: biogenic amines and related compounds in CSF", Neurology, 32(11):1299-1302 (1982).
Rye et al., "Modulation of vigilance in the primary hypersomnias by endogenous enhancement of GABAA receptors", Sci Transl Med., 4(161):161ra151 (2012).
Trotti et al., "Improvement in daytime sleepiness with clarithromycin in patients with GABA-related hypersomnia: Clinical experience", J Psychopharmacol., 28(7):697-702 (2014).
Written Opinion of the Internaitonal Searching Authority dated Jun. 10, 2015 (9 pages).
Roth, "The influence of cardiazol and psychoton on the EEG in narcolepsy", Chekh Fiziol., 3(4):420-423 (1954).
Roth et al., "L'EEG dans la narcolepsie-cataplexie", Electroencephalography and Clinical Neurophysiology, 16 (1-2):170-190 (1964) (in French, together with an English translation).
Supplemental European Search Report of corresponding European Application No. 15780466.7 dated Oct. 19, 2017 (5 pages).

(Continued)

*Primary Examiner* — Karl J Puttlitz
(74) *Attorney, Agent, or Firm* — Jones Day

(57) ABSTRACT

Provided herein are methods, formulations and dosing regimens for treating hypersomnia in a subject. For instance, methods provided herein comprise administering a $GABA_A$ chloride channel blocker. In certain embodiments, the $GABA_A$ chloride channel blocker is pentylenetetrazol (PTZ).

29 Claims, No Drawings

(56) References Cited

OTHER PUBLICATIONS

Wise et al., "Treatment of Narcolepsy and other Hypersomnias of Central Origin," Sleep, 2007, vol. 30, No. 12, pp. 1712-1727.
Dauvilliers et al., "Hypersomnia," Dialogues in Clinical Neuroscience, 2005, vol. 7, No. 4, pp. 347-356.
Kaneko et al., 1964, "Sedation threshold and metrazol threshold of narcoleptic patients," Folia Psychiatrica et Neurologica Japonica, 18(3)222-226.
Declaration of Dr. Russell Rosenberg, Ph.D., D.ABSM, Under 37 C.F.R. § 1.132 (including Exhibits 1-3), dated Mar. 10, 2020.
Declaration of Dr. Thomas Roth, Ph.D., Under 37 C.F.R. § 1.132 (including Exhibits 1-6), dated Mar. 22, 2020.
Ebert et al., 1997, "Differences in Agonist/Antagonist Binding Affinity and Receptor Transduction Using Recombinant Human γ-Aminobutyric Acid Type A Receptors," Molecular Pharmacology, 52:1150-1156.
Mignot, 2012, "A practical guide to the therapy of narcolepsy and hypersomnia syndromes," Neurotherapeutics, 9 (4):739-752.
Rye et al., 2017, "An open-label study of the efficacy, safety and tolerability of oral BTD-001 in adults with idiopathic hypersomnia or narcolepsy type 2," Sleep Medicine, Abstract, 40:e285-e286.
Trotti, 2016, "Flumazenil for the Treatment of Refractory Hypersomnolence: Clinical Experience with 153 Patients," Journal of Clinical Sleep medicine, 12(10):1389-1394.
Uusi-Oukari and Korpi, 2010, "Regulation of GABAA Receptor Subunit Expression by Pharmacological Agents," Pharmacol. Rev., 62(1):97-135.
Simmonds, "Classification of Some GABA Antagonists with Regard to Site of Action and Potency in Siices of Rat Cuneate Nucleaus," European Journal of Pharmacology. 1982, pp. 347-358, vol. 80.
Dauvilliers et al., "Absence of gamma-Aminobutync Acid-A Receptor Potentiation in Central Hypersomnolence Disorders." Annals of Neurology, 2016, pp. 259-268, vol. 80.

* cited by examiner

METHODS FOR TREATING HYPERSOMNIA

This application is a 371 national stage application of PCT/US2015/025696, filed Apr. 14, 2015, which claims priority to U.S. Provisional Application No. 61/979,918, filed Apr. 15, 2014, the contents of which are incorporated herein by reference in their entireties.

FIELD

Provided herein are methods for treating hypersomnia in a subject by administration of pentylenetetrazol (PTZ), as well as formulations and dosing regimens useful for treating hypersomnia.

BACKGROUND

Hypersomnia affects approximately 5% of the population and can burden affected individuals by, e.g., interfering with the ability to operate motor vehicles, socialize or maintain employment. It is a disorder characterized by excessive daytime sleepiness (EDS). Broadly classified, there are primary and secondary hypersomnias. Primary hypersomnias are believed to result from problems with an individual's brain functions that regulate sleep and wake. Primary hypersomnias are thought to occur independent of other underlying diseases or conditions. Secondary hypersomnias are believed to be caused by problems with night-time sleep, inability to get enough sleep or other medical problems that result in sleepiness, including, e.g., infections, depression, kidney failure, chronic fatigue syndrome, and neurodegenerative diseases such as Parkinson's disease and myotonic dystrophy. More specific classifications of hypersomnia include, e.g., the *International Classification of Sleep Disorders*—Second Edition (ICSD-2) (American Academy of Sleep Medicine, Westchester Ill. 2005) and the *Diagnostic and Statistical Manual of Mental Disorders*, $5^{th}$ Edition (DSM-V) (American Psychiatric Association, Washington D.C. 2013). Other publications describing clinical features of hypersomnia are, e.g., Ali et al., 2009, *J. Clin. Sleep Med.* 5, 562-568; Harris et al., 2012, *Neurol. Clin.* 30, 1027-1044.

Not much is known about the pathophysiology underlying primary hypersomnia. Researchers have suggested that, among other things, injury to adrenergic neurons or that decreased histamine levels may be associated with primary hypersomnia. See, e.g., Montplaisir et al., 1982, *Neurology* 32(11), 1299-302; Kanbayashi et al., 2009, *Sleep* 32(2), 181-7; Harris et al., 2012, *Neurol Clin* 30, 1027-104. Others have linked primary hypersomnia to an endogenous enhancement of type A gamma-aminobutyric acid ($GABA_A$) receptor activity in hypersomnia patients. See, e.g., Rye et al., 2012, *Sci. Tansl. Med.* 4, 161ra151 (pages 1-10); Trotti, et al., 2013, *J. Psychopharmacol.* 0269881113515062 [on-line publication], Kelty et al., 2014, *J. Psychopharmacol.*, 0269881114523865 [online publication].

Treatments for primary hypersomnia include stimulants and wake-promoting agents such as caffeine, amphetamines, modafinil, and armodafinil. See, e.g., Ali et al., 2009, *J. Clin. Sleep Med.* 5, 562-568; Harris et al., 2012, *Neurol Clin* 30, 1027-104. Potential treatments for GABA-related hypersomnia have been described in publications such as Parker et al., U.S. Patent Application Publication No. US 2011/0028418 A1, published Feb. 3, 2011; Trotti, et al., 2013, *J. Psychopharmacol.* 0269881113515062 [online publication], Kelty et al., 2014, *J. Psychopharmacol.*, 0269881114523865 [online publication].

Treatments for hypersomnia that can, e.g., be orally administered, lack undesirable side-effects or are not habit-forming when taken, are desired.

BRIEF SUMMARY

Provided herein are methods for treating a hypersomnia in a subject including administering pentylenetetrazol (PTZ) to the subject having hypersomnia, wherein the administering is effective to treat the hypersomnia.

In some embodiments, the PTZ is administered at least once daily for at least five consecutive days.

In some embodiments, the PTZ antagonist is administered once a day, twice a day, three times a day or four times a day.

In some embodiments, the PTZ is administered at a dose of about 1 mg to 1,500 mg.

In some embodiments, the PTZ is administered at a dose of about 5 mg to 1,000 mg.

In some embodiments, the PTZ is administered at a dose of about 10 mg to 800 mg.

In some embodiments, the PTZ is administered at a dose of about 25 mg to 600 mg.

In some embodiments, the PTZ is administered at a dose sufficient to achieve a mean Cmax of about 25 to 25,000 ng/ml.

In some embodiments, the PTZ is administered at a dose sufficient to achieve a mean Cmax of about 50 to 20,000 ng/ml.

In some embodiments, the PTZ is administered at a dose sufficient to achieve a mean Cmax of about 100 to 15,000 ng/ml.

In some embodiments, the PTZ is administered at a dose sufficient to achieve a mean Cmax of about 500 to 10,000 ng/ml.

In some embodiments, the PTZ is administered at a dose sufficient to achieve a mean Cmax of about 1,000 to 8,000 ng/ml.

In some embodiments, the PTZ is administered at a dose sufficient to achieve a mean Cmax of about 3,000 to 6,000 ng/ml.

In some embodiments, the PTZ is administered at a dose sufficient to achieve a mean Cmax of about 300 to 3,000 ng/ml.

In some embodiments, the PTZ is administered at a dose sufficient to achieve a mean Cmax of about 500 to 3,000 ng/ml.

In some embodiments, the PTZ is administered at a dose sufficient to achieve a mean Cmax of about 1,000 to 3,000 ng/ml.

In some embodiments, the PTZ is administered at a dose sufficient to achieve a mean Cmax of about 2,000 to 3,000 ng/ml.

In some embodiments, the PTZ is administered prior to or during the subject's night-time sleep. In some embodiments, the PTZ is administered prior to or during the subject's morning wake-up period.

In some embodiments, the Cmax is achieved in the brain.

In some embodiments, the PTZ is administered in an oral formulation

In some embodiments, the PTZ is administered in a delayed release formulation. In certain embodiments, the delayed release formulation delays the peak concentration of PTZ in brain by 30 minutes to 12 hours from the time of administration. In some embodiments, the delayed release formulation releases PTZ during the subject's night-time sleep or morning wake-up period.

In some embodiments, the PTZ is administered in a sustained release formulation. In certain embodiments, the sustained release formulation maintains a therapeutically effective dose of the PTZ for 30 minutes to 12 hours after administration.

In some embodiments, the PTZ is formulated to achieve an AUC of about 500 ng*hr/mL to 150,000 ng*hr/mL.

In some embodiments, the PTZ is formulated to achieve an AUC of about 1,000 ng*hr/mL to 100,000 ng*hr/mL.

In some embodiments, the PTZ is formulated to achieve an AUC of about 5,000 ng*hr/mL to 50,000 ng*hr/mL.

In some embodiments, the PTZ is formulated to achieve an AUC of about 10,000 ng*hr/mL to 20,000 ng*hr/mL.

In some embodiments, the PTZ is formulated to achieve an AUC of about 1,000 ng*hr/mL to 15,000 ng*hr/mL.

In some embodiments, the PTZ is formulated to achieve an AUC of about 2,500 ng*hr/mL to 12,500 ng*hr/mL.

In some embodiments, the PTZ is formulated to achieve an AUC of about 5,000 ng*hr/mL to 10,000 ng*hr/mL.

In some embodiments, the PTZ is formulated to achieve an AUC of about or about 7,500 ng*hr/mL to 12,000 ng*hr/mL.

In some embodiments, the subject is human.

In some embodiments, the cerebrospinal fluid (CSF) of the subject having the hypersomnia comprises elevated levels of an endogenous positive $GABA_A$ receptor allosteric modulator relative to the CSF of a subject not having the hypersomnia.

In some embodiments, the hypersomnia syndrome is mediated by an endogenous positive allosteric $GABA_A$ receptor modulator in the subject.

In some embodiments, the hypersomnia is a primary hypersomnia.

In some embodiments, the hypersomnia is a type selected from the group consisting of idiopathic hypersomnia, recurrent hypersomnia, shift work sleeping disorder, restless leg syndrome, nocturnal dystonia, nocturnal movement disorder, Klein-Levin syndrome, Parkinson's disease, excessive sleepiness, obstructive sleep apnea, REM behavior disorder, endozepine related recurrent stupor, frontal nocturnal dystonia, norturnal movement disorder, narcolepsy, and amphetamine resistant hypersomnia.

In some embodiments, the hypersomnia is an idiopathic hypersomnia.

In some embodiments, the hypersomnia is narcolepsy without cataplexy.

In some embodiments, the hypersomnia is narcolepsy type 1 (with cataplexy).

In some embodiments, the subject having hypersomnia is assessed according to the Stanford Sleepiness Scale (SSS), the Epworth Sleepiness Scale (ESS), the multiple sleep latency (MSL) test, maintenance of wakefulness test (MWT), objective psychomotor vigilance (PVT) tasks, the Functional Outcomes of Sleep Questionnaire (FOSQ), the Multidimensional Fatigue Inventory (MFI), the Clinical Global Impression of Severity (CGI-S), the Clinical Global Impression of Change (CGI-C), the Beck Depression Inventory (BDI-II), self-reported fogginess scores, self-reported mood scores or self-reported sleepiness scores.

In some embodiments, the subject having hypersomnia improves by at least about 2 points on the ESS, at least about 2 min for sleep onset latency on MWT, at least about 8 points on the FOSQ, at least about 4 points on one or more MFI scales, at least one point on CGI-S or CGI-C, at least about 4 points on the BDI-II, or at least about 1.0 point on a self-reported fogginess score.

In some embodiments, PTZ is administered twice daily at a dose of 100 mg for a period of at least one week.

In another aspect, provided herein are methods for treating fatigue, tiredness or fogginess in a subject including administering a $GABA_A$ chloride channel blocker to the subject having fatigue, tiredness or fogginess, wherein the administering is effective to treat the fatigue, tiredness or fogginess. In some embodiments, fatigue can include, e.g., general fatigue, physical fatigue, or mental fatigue.

In some embodiments, the methods include assessing efficacy of the $GABA_A$ chloride channel blocker in the treatment of fatigue by assessing fatigue in the subject using the Multidimensional Fatigue Inventory (MFI).

In another aspect, provided herein are methods for treating a hypersomnia, fatigue, tiredness or fogginess in a subject including selecting a subject having hypersomnia, fatigue, tiredness or fogginess; administering a $GABA_A$ chloride channel blocker to the subject having hypersomnia, fatigue, tiredness or fogginess, wherein the administering is effective to treat the hypersomnia, fatigue, tiredness or fogginess, and, optionally, assessing the efficacy of the $GABA_A$ chloride channel blocker in treating the hypersomnia, fatigue, tiredness or fogginess.

In another aspect, provided herein are uses of a $GABA_A$ chloride channel blocker for the treatment of a hypersomnia, fatigue, tiredness or fogginess in a patient. In some embodiments, the $GABA_A$ chloride channel blocker is PTZ.

Terminology

The term "pharmaceutically acceptable" as used herein refers to a component that is compatible with other ingredients of a pharmaceutical composition or formulation and is suitable for use in contact with tissues of a subject without undue toxicity, irritation, allergic response, immunogenicity or other complications, commensurate with a reasonable benefit/risk ratio.

As used herein, the abbreviation "GABA" refers to gamma-aminobutyric acid.

As used herein, the abbreviation "$GABA_A$" refers to a type A gamma-aminobutyric acid receptor.

A "subject" as used herein means an animal, preferably a mammal, including, for example, mouse, rat, rabbit, dog, cat, guinea pig, goat, cow, horse, pig, sheep, monkey, primate, ape, or human. The term "individual" as used herein is when the subject is a human.

The term "PTZ derivative," as used herein, refers to any structural analog of PTZ. Examples of PTZ derivatives are described for example in International patent application No. PCT/US2012/036217 (published as WO 2012/151343). In some embodiments, PTZ derivatives have increased metabolic stability as compared to PTZ. PTZ derivatives with increased metabolic stability can, in certain embodiments, provide therapeutic benefits over PTZ, for instance, by (a) enhancing subject compliance by decreasing the number of doses needed to achieve the therapeutic effect of PTZ, (b) decreasing the amount of a dose needed to achieve the therapeutic effect of PTZ and/or reduce the occurrence of potential adverse events, (c) creating a more effective drug and/or a safer drug for polypharmacy, whether the polypharmacy be intentional or not, and/or (d) attenuating interpatient variability due to polymorphisms in enzymes that normally metabolize PTZ.

The term "peak concentration" as used herein refers to the maximum concentration of a compound, e.g., a GABA-A receptor antagonist, that occurs after being administered to a subject. In various embodiments, the peak concentration can, for example, be in the subject's blood, plasma, brain, cerebrospinal fluid, etc. A peak concentration can, for instance, be a Cmax.

The term "area under the curve (AUC)," as used herein, refers to the area under the curve in a plot of blood plasma concentration of a $GABA_A$ chloride channel blocker against time. In certain embodiments, the AUC is computed starting at the time of administration of the $GABA_A$ chloride channel blocker and ending when the plasma concentration of the $GABA_A$ chloride channel blocker is negligible. In certain embodiments, the plasma concentration of the $GABA_A$ chloride channel blocker is measured at discrete time-points and the AUC is mathematically approximated, e.g., using the trapezoidal rule.

The term "dosing regimen" as used herein refers to a specified amount of compound administered per time unit and duration of dosing (e.g., 3 times/day for 7 days).

DETAILED DESCRIPTION

In one aspect provided herein are methods for treating a hypersomnia in a subject comprising administering a $GABA_A$ chloride channel blocker to the subject having hypersomnia, wherein the administering is effective to treat the hypersomnia.

In some embodiments, the hypersomnia is a primary hypersomnia. In some embodiments, the hypersomnia is an idiopathic hypersomnia (IHS). In some embodiments, the hypersomnia is narcolepsy. In some embodiments, the hypersomnia is narcolepsy without cataplexy.

In some embodiments, the hypersomnia is Narcolepsy Type I (with cataplexy).

In some embodiments, the hypersomnia is an insomnia disorder according to the Diagnostic and Statistical Manual of Mental Disorders, 5$^{th}$ Edition (DSM-V), 361-422, which are hereby incorporated herein in their entirety. In some embodiments, the hypersomnia is an intrinsic sleep disorder according to the *International Classification of Sleep Disorders International Classification of Sleep Disorders, Revised: Diagnostic and Coding Manual*© 2001 American Academy of Sleep Medicine, ISBN 0-9657220-1-5, pages 27-72 (Intrinsic Sleep Disorders), which are hereby incorporated herein in their entirety.

In some embodiments, the hypersomnia is GABA-related.

A GABA-related hypersomnia can, for instance, be characterized in a subject with the hypersomina by excessive $GABA_A$ receptor activity caused by a concentration of a $GABA_A$ receptor modulator in the cerebrospinal fluid (CSF) that is greater relative to the concentration of people that do not have hypersomnia.

In certain embodiments, the hypersomnia is mediated by an endogenous positive allosteric $GABA_A$ receptor modulator in the CSF of the subject. In certain embodiments, the positive allosteric $GABA_A$ receptor modulator is trypsin-sensitive. In certain embodiments, the positive allosteric $GABA_A$ receptor modulator has a molar mass of 500-3,000 Dalton.

In certain embodiments, the hypersomnia is a secondary hypersomnia.

In some embodiments, the hypersomnia treated in the methods provided herein is a recurrent hypersomnia, shift work sleeping disorder, restless leg syndrome, nocturnal dystonia, nocturnal movement disorder, Klein-Levin syndrome, Parkinson's disease, excessive sleepiness, obstructive sleep apnea, REM behavior disorder, endozepine related recurrent stupor, frontal nocturnal dystonia, norturnal movement disorder, narcolepsy, and amphetamine resistant hypersomnia.

In some embodiments, the $GABA_A$ chloride channel blocker is selected from the group consisting of pentylenetetrazole (PTZ), bilobalide (BB), penicillin and ginkgolide B.

Without being limited by any theory, it is believed that $GABA_A$ chloride channel blockers are superior in the treatment of hypersomnia as compared to $GABA_A$ receptor antagonists that are not $GABA_A$ chloride channel blockers. For example, the $GABA_A$ chloride channel blocker PTZ is demonstrated in the examples herein to have superior effects in the treatment of hypersomnia as compared to the allosteric $GABA_A$ antagonist, flumazenil, which binds to the benzodiazepine binding site of the $GABA_A$ receptor, or as compared to other putative $GABA_A$ antagonists, such as clarithromycin.

In certain embodiments, the $GABA_A$ chloride channel blocker is PTZ.

In certain embodiments, the $GABA_A$ chloride channel blocker is a pharmaceutically acceptable salt of PTZ, BB, penicillin, or ginkgolide B.

In certain embodiments, the $GABA_A$ chloride channel blocker is a derivative of PTZ, BB, penicillin or ginkgolide B.

In certain embodiments, the $GABA_A$ chloride channel blocker is a derivative of PTZ, for example, a deuterated PTZ. In other embodiments, the PTZ derivative is a fluorinated PTZ. In certain embodiments the $GABA_A$ chloride channel blocker is a PTZ derivative described in International patent application No. PCT/US2012/036217 (published as WO 2012/151343), which is hereby incorporated by reference herein in its entirety.

In another aspect, provided herein are methods for treating a hypersomnia in a subject comprising administering a $GABA_A$ antagonist to the subject having hypersomnia, wherein the administering is effective to treat the hypersomnia.

In some embodiments the $GABA_A$ antagonist is a $GABA_A$ chloride channel blocker.

In some embodiments, the $GABA_A$ antagonist is an inverse agonist.

$GABA_A$ receptor subtypes have distinct patterns of expression, biophysical properties, and pharmacology. For example, the α5 subtype constitutes only around 5% to 10% of total brain $GABA_A$ receptors; yet within the hippocampus, this subtype comprises around 25%. It can thus be expected that a $GABA_A$ chloride channel blocker that has higher affinity and/or efficacy for the α5 subtype would exert its function primarily in certain areas of the brain or certain neurons and less in others, giving rise to specific effects. The specific effect may be deduced from the localization of particular subtypes of the $GABA_A$ receptor in the brain, or it may be determined experimentally.

In some embodiments, the $GABA_A$ antagonist has comparable affinity and/or efficacy to each of the various subtypes of the $GABA_A$ receptor and thus produces quantitatively similar reductions of the inhibitory effects of $GABA_A$ on the various subtypes of the $GABA_A$ receptor ("nonselective $GABA_A$ antagonist"). In other embodiments, the $GABA_A$ antagonist has different affinity and/or efficacy to the various subtypes of the $GABA_A$ receptor and thus produces quantitatively different reductions of the inhibitory effects of $GABA_A$ on the various subtypes of the $GABA_A$ receptor ("selective $GABA_A$ antagonist"). Such quantitatively different reductions of the inhibitory effects of GABA$_A$ on the various subtypes of the GABA$_A$ receptor of a selective GABA$_A$ receptor antagonist may result in specific effects that include but are not limited to increases in wakefulness and decreases in daytime sleepiness. Examples of GABA$_A$ antagonists that have greater affinity and/or efficacy for the α5 subtype than for the α1, α2 or α3 subtypes include but are not limited to Ro 15-4513, L-655, 708, RY-080 (Skolnick et al. 1997 *J. Pharmacol. Exp. Ther.* 283:488-93), PWZ-029 (8-chloro-3-methoxymethyl)-5-methyl-4H-imidazo[1,5-a][1,4]benzodiazepin-6-one), RO4938581 (Ballard et al. 2009 *Psychopharmacology* 202:207-23), α5IA (3-(5-methylisoxazol-3-yl)-6-[(1-methyl-1H-1,2,3-triazol-4-yl)methoxy][1,2,4]triazolo[3,4-a]phthalazine), NGD 97-1 (CP-457,920; Bednar et al. 2004 *Clin. Pharmacol. Ther.* 75:P30), MRK-536 (Chambers et al. 2002 *J. Med. Chem.* 45:1176-79; Chambers et al. 2003 *Med. Chem.* 46:2227-40; Atack et al. 2011 *Curr. Top. Med. Chem.* 11(9):1203-14), MRK-016 (Chambers et al. 2004 *J. Med. Chem.* 47:5829-32), RY-023, S-8510 ([2-(3-isoxazolyl)-3,6,7,9-tetrahydroimidazo[4,5-d]pyran[4,3-b]pyridine monophosphate monohydrate), RY-80, AC-3933 (5-(3-methoxyphenyl)-3-(5-methyl-1,2,4-oxadiazol-3-yl)-2-oxo-1,2-dihydro-1,6-naphthyridine), certain benzothiophene derivatives (Chambers et al., 2003 *J. Med. Chem.* 46 (11): 2227-40), certain triazolophthalazine derivatives (Steinfeld et al. 2004 *J. Med. Chem.* 47(9):2176-9; Street et al. 2004 *J. Med. Chem.* 47(14):3642-57), certain pyrazolotriazine derivatives (Chambers et al. 2004 *J. Med. Chem.* 47(24): 5829-32), and RG1662.

In some embodiments of the methods for treating a hypersomnia, the GABA$_A$ antagonist administered to the subject having hypersomnia is a GABA$_A$ chloride channel blocker.

In some embodiments, the subject is human.

The subject may be of any age. For instance, a human subject may be an adult or a child (e.g., a neonate, infant, young child, adolescent). In some embodiments, the subject is in the mid-to-late teens or early twenties.

In some embodiments, the subject has hypersomnia from childhood onwards. In other embodiments, the subject develops hypersomnia with progressing age.

In some such embodiments, the subject has idiopathic hypersomnia.

In some embodiments, the subject exhibits pervasive daytime sleepiness despite adequate, or more typically, extraordinary sleep amounts (e.g., >10 hours per night). In some embodiments, the subject exhibits unrefreshing or non-restorative sleep. In some embodiments, the subject exhibits sleep inertia. In some embodiments, the subject exhibits sleep drunkenness (difficulty awakening from sleep, accompanied by feelings of grogginess and disorientation upon awakening). In some embodiments, the subject is an individual describing sleep as "deep" and who finds arousal from sleep difficult, e.g., requiring multiple alarm clocks. In some embodiments, daytime naps of the subject are on the scale of hours (e.g., more than 1 hour, 2 hours, 3 hours, 4 hours or 5 hours) and are experienced as unrefreshing. In some embodiments, the subject exhibits hypersensitivity to sedating medications such as anesthetics, sleeping pills, or alcohol.

In another aspect, provided herein are methods for treating fatigue, tiredness or fogginess in a subject comprising administering a GABA$_A$ chloride channel blocker to the subject having fatigue, tiredness or fogginess, wherein the administering is effective to treat the fatigue, tiredness or fogginess. In some embodiments, fatigue can include, e.g., general fatigue, physical fatigue, or mental fatigue. In some embodiments, the methods comprise assessing efficacy of the GABA$_A$ chloride channel blocker in the treatment of fatigue by assessing fatigue in the subject using the Multidimensional Fatigue Inventory (MFI).

In another aspect, provided herein are methods for treating a hypersomnia, fatigue, tiredness or fogginess in a subject comprising selecting a subject having hypersomnia, fatigue, tiredness or fogginess; administering a GABA$_A$ chloride channel blocker to the subject having hypersomnia, fatigue, tiredness or fogginess, wherein the administering is effective to treat the hypersomnia, fatigue, tiredness or fogginess, and, optionally, assessing the efficacy of the GABA$_A$ chloride channel blocker in treating the hypersomnia, fatigue, tiredness or fogginess.

In some embodiments, the subject having hypersomnia, fatigue, tiredness or fogginess has elevated levels or activities of an endogenous positive GABA$_A$ receptor allosteric modulator relative to the CSF of a subject not having hypersomnia, fatigue, tiredness or fogginess.

In some embodiments, the subject having hypersomnia, fatigue, tiredness or fogginess failed to respond, responded only partially, or was been unable to tolerate a GABA$_A$ receptor antagonist other than a GABA$_A$ chloride channel blocker prior to administration of the GABA$_A$ chloride channel blocker. In some embodiments, the subject having hypersomnia, fatigue, tiredness or fogginess failed to respond, responded only partially, or was unable to tolerate a GABA$_A$ receptor antagonist other than PTZ prior to administration of PTZ. In some embodiments, the subject having hypersomnia, fatigue, tiredness or fogginess failed to respond to flumazenil or clarithromycin prior to administration of PTZ.

In some embodiments, the subject having hypersomnia, fatigue, tiredness or fogginess responds better to a GABA$_A$ chloride channel blocker than to a GABA$_A$ receptor antagonist other than a GABA$_A$ chloride channel blocker. In some embodiments, the subject having hypersomnia, fatigue, tiredness or fogginess responds better to a PTZ than to a GABA$_A$ receptor antagonist other than PTZ. In some embodiments, the subject having hypersomnia, fatigue, tiredness or fogginess responds better to a PTZ than to flumazenil or clarithromycin.

In yet other embodiments provided herein are methods to improve clarity of thinking comprising administering PTZ to a subject in need thereof.

In some embodiments, ESS Total Score of the subject having hypersomnia, fatigue, tiredness or fogginess is at least 2 points, at least 3 points, at least 4 points, or at least 5 point lower after administration of PTZ than after administration of flumazenil or clarithromycin to the subject having hypersomnia, fatigue, tiredness or fogginess.

In some embodiments, the FOSQ Total Score of the subject having hypersomnia, fatigue, tiredness or fogginess is at least 2 points, at least 3 points, at least 4 points, or at least 5 point higher after administration of PTZ than after administration of flumazenil or clarithromycin to the subject having hypersomnia, fatigue, tiredness or fogginess.

In some embodiments, an MFI score (e.g., General Fatigue Scale, Physical Fatigue Scale, Reduced Activity Scale, Reduced Motivation Scale, Mental Fatigue Scale) of the subject having hypersomnia, fatigue, tiredness or fogginess is at least 2 points, at least 3 points, at least 4 points, or at least 5 point lower after administration of PTZ than after administration of flumazenil or clarithromycin to the subject having hypersomnia, fatigue, tiredness or fogginess.

In some embodiments, the CGI-S or CGI-C score of the subject having hypersomnia, fatigue, tiredness or fogginess is at least 1 point, at least 2 points, at least 3 points, or at least 4 points lower after administration of PTZ than after administration of flumazenil or clarithromycin to the subject having hypersomnia, fatigue, tiredness or fogginess.

In some embodiments, the cerebrospinal fluid (CSF) of the subject having hypersomnia has elevated levels or activities of an endogenous positive GABA$_A$ receptor allosteric modulator relative to the CSF of a subject not having hypersomnia. The cell-based patch clamp assay described in Rye et al., 2012, *Sci. Tansl. Med.* 4, 161ra151, page 2, can be used to compare relative levels or activities of GABA$_A$ receptor allosteric modulator in CSF samples from those with hypersomnia and those not having hypersomnia.

In certain embodiments the subject is an animal. In some embodiments, the subject is an animal model for hypersomnia.

In some embodiments, a single dose of the GABA$_A$ chloride channel blocker is administered to the subject at one time. In other embodiments, multiple doses of the GABA$_A$ chloride channel blocker are given to the subject over a period of time (e.g., over a period of hours, days, weeks, months, or even years). For certain routes of administration (e.g., transdermal), administration is continuous.

It is understood that the precise dosage, timing of administration, and duration of treatment may vary with the age, weight, gender, and medical condition of the subject, as well as the severity of the hypersomnia, the route of administration, the level of metabolic and excretory function of the subject, the dosage form employed, and the particular GABA$_A$ chloride channel blocker administered. Dosage, timing of administration and duration of treatment may be determined empirically by one of ordinary skill in the art using known testing protocols, or by extrapolation from in vivo or in vitro tests or diagnostic data.

GABA$_A$ chloride channel blockers provided herein may cause epileptic activity, and thus doses should be well below a dose that will induce seizures. It is further understood that for any particular subject, specific dosage regimens can be adjusted over time according to the individual need and the professional judgment of the person administering or supervising the administration of the GABA$_A$ chloride channel blocker.

PTZ has been reported to cause seizures in humans. See, e.g., Redlich, 1939, Am J. Psychiatry 96, 193-204. In some embodiments, doses of PTZ are below seizure inducing doses. When administered at doses approaching seizure inducing doses PTZ should be administered under supervision of a medical professional. Without wishing to be bound by theory, it is believed that seizure inducing doses of PTZ are higher in humans with hypersomnia than in humans without hypersomnia. The higher seizure inducing doses of PTZ in humans with hypersomnia are due to elevated levels of a positive allosteric GABA$_A$ modulator, which is detectable, e.g., in the CSF of the humans with hypersomnia.

In certain embodiments, a therapeutically effective amount of the GABA$_A$ chloride channel blocker, e.g., PTZ or PTZ derivative, is administered to the subject having hypersomnia.

The dosage and dosing regimen for the administration of the GABA$_A$ chloride channel blocker, as provided herein, is also influenced by toxicity in relation to therapeutic efficacy. Toxicity and therapeutic efficacy can be determined according to standard pharmaceutical procedures in cell cultures and/or experimental animals, including, for example, determining the LD50 (the dose lethal to 50% of the population, or, alternatively, for the methods provided herein, the dose that kindles or induces seizures in 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are generally preferred.

In some embodiments, administration of the GABA$_A$ chloride channel blocks GABA$_A$ chloride channel only in the areas of the subject's brain affecting the sleep-wakefulness cycle (e.g., the thalamus or reticular activating system, RAS) because the compound is specifically delivered to such a brain region in the subject (e.g., via a device that is implanted in or near the hypothalamus or RAS, or via molecular cues).

In some embodiments, the GABA$_A$ chloride channel blocker is administered at a particular point of the circadian cycle of the subject. Such circadian cycle sensitive dosing aims to target the compound or pharmaceutical composition to the portions of the circadian cycle of a subject during which disease progression, symptoms, risk, or treatment efficacy are highest. Circadian cycle sensitive dosing can offer the potential for efficacy at lower doses to provide a larger therapeutic window relative to doses that cause side effects. In some embodiments, the GABA$_A$ chloride channel blocker is administered so that therapeutic levels of the GABA$_A$ chloride channel blocker or of an active metabolite of the GABA$_A$ chloride channel blocker in the brain of the subject are achieved during the portion of the circadian cycle when the subject sleeps. In some such embodiments, the GABA$_A$ chloride channel blocker is administered in the morning. In other such embodiments, the GABA$_A$ chloride channel blocker is administered in the evening. In some embodiments, the GABA$_A$ chloride channel blocker the compound is administered between 6 am and 12 pm. In some embodiments, the GABA$_A$ chloride channel blocker is administered between 6 pm and 12 am. In some embodiments, the GABA$_A$ chloride channel blocker is administered during the sleep cycle of the subject. In some embodiments, the GABA$_A$ chloride channel blocker is administered to subject in a form (e.g., delayed release or sustained release or other suitable form) that will result in a peak concentration occurring in the subject while the subject is asleep.

The GABA$_A$ chloride channel blocker is administered in a single daily dose, or the total daily dose may be administered in divided doses, two, three, or more times per day. In some embodiments, the dosing regimen is maintained for at least about two days, at least about one week, at least about two weeks, at least about three weeks, at least about one month, or longer. In some embodiments, an intermittent dosing regimen is used, i.e., once a month, once every other week, once every other day, once per week, twice per week, and the like. In some embodiments, the GABA$_A$ chloride channel blocker is administered at least once daily for at least five consecutive days.

In some embodiments, the GABA$_A$ chloride channel blocker is administered at an initial low dose followed by one or more subsequent doses higher than the initial low dose. In some embodiments, the GABA$_A$ chloride channel blocker is administered at an initial high dose followed by one or more subsequent maintenance doses lower than the initial high dose. In some embodiments, the GABA$_A$ chloride channel blocker is administered in one or more cycles. In certain embodiments, the cycles of GABA$_A$ chloride channel blocker administration are about 1 day cycles, 2 day cycles, 3 day cycles, 4 day cycles, 5 day cycles, 6 day cycles, 1 week cycles, 2 week, 4 week cycles, 6 week cycles, or 3 month cycles. Typically, the cycles of GABA$_A$ chloride channel blocker administration are about 1 week cycles. In some embodiments, two or more cycles of administration of the GABA$_A$ chloride channel blocker are separated by a drug holiday. In certain embodiments, drug holidays last about 1 day, 2 days, 3 days, 4 days, 5 days, 6 days, 1 week, 2 weeks or 4 weeks.

In some embodiments, an effective dose of the GABA$_A$ chloride channel blocker will transiently reduce the chloride influx at GABA$_A$ receptors in the central nervous system, for example for a period of at least about 1 minute, at least about 5 minutes, at least about 30 minutes, at least about 1 hours, or more, usually not more than about 4 hours, not more than about 3 hours, or not more than about 2 hours. However, there may also be embodiments where the effective dose provides for a longer lasting reduction of chloride ion influx at GABA$_A$ receptors in the central nervous system, for example for at least about 5 hours, at least about 6 hours, at least about 7 hours, at least about 8 hours, at least about 9 hours, at least about 10 hours, at least about 11 hours, at least about 12 hours, or longer. Such embodiments may provide for a more continuous activity profile, for example by using a continuous pump or by administering an effective dose more than once a day (e.g., twice, three times, four times, and more per day).

The GABA$_A$ chloride channel blocker, can, for example, be administered to the subject as a pharmaceutical composition that includes an effective amount of the GABA$_A$ chloride channel blocker in a pharmaceutically acceptable vehicle. It can be incorporated into a variety of formulations for therapeutic administration by combination with appropriate pharmaceutically acceptable carriers or diluents, and may be formulated into preparations in solid, semi-solid, liquid, or gaseous forms, such as tablets, capsules, powders, granules, ointments, solutions, suppositories, injections, inhalants, gels, microspheres, and aerosols.

In some embodiments, the GABA$_A$ chloride channel blocker is formulated as a delayed release formulation. Suitable pharmaceutical excipients and unit dose architecture for delayed release formulations may include those described in U.S. Pat. Nos. 3,062,720 and 3,247,066. Delayed release formulations can be formulated in tablets that can be coated using known methods to achieve delayed disintegration in the gastrointestinal tract of a human. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Oral compositions that specifically release orally-administered agents in the small or large intestines of a human patient can be made using known technology. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon. See Hardy et al. 1987 Aliment Pharmacol. Ther. 1:273-80. Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend & Chang 1984 J. Med. Chem. 27:261-6) and a variety of naturally available and modified polysaccharides (see PCT application PCT/GB89/00581) can be used in such formulations.

In certain embodiments, the delayed release formulation delays the peak concentration of PTZ in brain by 30 minutes to 12 hours from the time of administration. In some embodiments, the delayed release formulation releases PTZ during the subject's night-time sleep or morning wake-up period.

In other embodiments, the GABA$_A$ chloride channel blocker is formulated as a sustained release formulation. Suitable pharmaceutical excipients and unit dose architecture for sustained release formulations include those described in U.S. Pat. Nos. 3,062,720 and 3,247,066. The compound that can reduce neuronal inhibition either in its free form or as a salt can be combined with a polymer such as polylactic-glycoloic acid (PLGA), poly-(I)-lactic-glycolic-tartaric acid (P(I)LGT) (WO 01/12233), polyglycolic acid (U.S. Pat. No. 3,773,919), polylactic acid (U.S. Pat. No. 4,767,628), poly(ε-caprolactone) and poly(alkylene oxide) (U.S. 20030068384) to create a sustained release formulation. Such formulations can be used in implants that release an agent over a period of several hours, a day, a few days, a few weeks, or several months depending on the polymer, the particle size of the polymer, and the size of the implant (see, e.g., U.S. Pat. No. 6,620,422). Other sustained release formulations are described in EP 0 467 389 A2, WO 93/241150, U.S. Pat. No. 5,612,052, WO 97/40085, WO 03/075887, WO 01/01964A2, U.S. Pat. No. 5,922,356, WO 94/155587, WO 02/074247A2, WO 98/25642, U.S. Pat. Nos. 5,968,895, 6,180,608, U.S. 20030171296, U.S. 20020176841, U.S. Pat. Nos. 5,672,659, 5,893,985, 5,134,122, 5,192,741, 5,192,741, 4,668,506, 4,713,244, 5,445,832 4,931,279, 5,980,945, WO 02/058672, WO 9726015, WO 97/04744, and US20020019446. In such sustained release formulations microparticles of drug are combined with microparticles of polymer. One or more sustained release implants can be placed in the large intestine, the small intestine, or both. U.S. Pat. No. 6,011,011 and WO 94/06452 describe a sustained release formulation providing either polyethylene glycols (where PEG 300 and PEG 400 are most preferred) or triacetin. WO 03/053401 describes a formulation that may both enhance bioavailability and provide controlled release of the agent within the GI tract. Additional sustained release formulations are described in WO 02/38129, EP 326 151, U.S. Pat. No. 5,236,704, WO 02/30398, WO 98/13029; U.S. 20030064105, U.S. 20030138488A1, U.S. 20030216307A1, U.S. Pat. No. 6,667,060, WO 01/49249, WO 01/49311, WO 01/49249, WO 01/49311, and U.S. Pat. No. 5,877,224.

In certain embodiments, a delayed release formulation is such that the peak concentration of the GABA$_A$ chloride channel blocker occurs in the subject by 30 minutes to 8 hours from the time of administration. In certain embodiments, the delayed release formulation delays the peak in the subject's blood or in the subject's brain by 30 minutes to 1 hour, by 1 hour to 4 hours, or by 4 hours to 8 hours, from the time of administration.

In certain embodiments, a sustained release formulation is such that a peak concentration of the GABA$_A$ chloride channel blocker is maintained in the subject for 30 minutes to 8 hours after being administered to the subject. In certain embodiments, the sustained release formulation maintains a peak in the subject's blood or in the subject's brain for 30 minutes to 60 minutes, for 1 hour to 4 hours, or for 4 hours to 8 hours, after administration to the subject.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients, and the like. The compositions can also include additional substances to approximate physiological conditions, such as pH adjusting and buffering agents, toxicity adjusting agents, wetting agents, and detergents. The composition can also include any of a variety of stabilizing agents, such as an antioxidant for example. Tablet formulations can comprise a sweetening agent, a flavoring agent, a coloring agent, a preservative, or some combination of these to provide a pharmaceutically elegant and palatable preparation. Further guidance regarding formulations that are suitable for various types of administration can be found in Remington's Pharmaceutical Sciences, Mace Publishing 20 Company, Philadelphia, Pa., 17th ed. (1985).

For oral administration, the $GABA_A$ chloride channel blocker can be administered in solid dosage forms, such as capsules, tablets, and powders, or in liquid dosage forms, such as elixirs, syrups, and suspensions. The compound can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

In some embodiments, the method comprises the step of administering to the subject PTZ at a dose of between 0.005 mg/kg and 25 mg/kg, between 0.01 mg/kg and 10 mg/kg, between 0.001 mg/kg and 0.2 mg/kg, between 0.01 mg/kg and 2 mg/kg, between 0.03 mg/kg and 6 mg/kg, or between 0.05 mg/kg and 0.5 mg/kg.

In some embodiments, the method comprises the step of administering to the subject PTZ at a dose of about 25 mg/kg of patient weight, about 20 mg/kg, about 10 mg/kg, about 5 mg/kg, about 3 mg/kg, about 1 mg/kg, about 0.3 mg/kg, about 0.1 mg/kg, about 0.05 mg/kg, about 0.025 mg/kg, or about 0.01 mg/kg.

In some embodiments, the method comprises the step of administering to the subject PTZ at a daily dose of from 0.1 mg/day to 5 gm/day, from 1 mg/day to 1 g/day, or from 3 mg/day to 300 mg/day. In various embodiments, the administered dose is about 1.5 gm, about 1.25 gm, about 1 gm, about 750 mg, about 500 mg, about 250 mg, about 200 mg, about 100 mg, about 50 mg, about 25 mg, about 10 mg, about 5 mg, about 1 mg, about 0.5 mg, about 0.25 mg, or about 0.05 mg.

In some embodiments, the method comprises the step of administering to the subject PTZ at a dose of about 1 mg to 5 gm, about 1 mg to 3 gm, about 1 mg to 2 gm, about 1 mg to 1.5 gm, about 1 mg to 1.25 gm, about 5 mg to 1 gm, about 10 to 800 mg, about 25 mg to 600 mg, about 50 mg to 400 mg, or about 100 mg to 200 mg. In some embodiments, the method comprises the step of administering to the subject PTZ at a dose of about 5 gm, about 4 gm, about 3 gm, about 2 gm, about 1.5 gm, about 1.25 gm, about 1 gm, about 750 mg, about 500 mg, about 250 mg, about 200 mg, about 100 mg, about 50 mg, about 25 mg, about 10 mg, about 5 mg, about 1 mg, about 0.5 mg, about 0.25 mg, or about 0.05 mg.

In some embodiments the dose of PTZ is a daily dose, a weekly dose, a biweekly dose or a monthly dose. In some embodiments, the dose of PTZ is administered as a unit dose (e.g., in a capsule). In some embodiments, the dose of PTZ is administered in an implantable device. In various embodiments, the dose of PTZ is released from the implantable device over a period of time. In certain embodiments, the period of time is more than 6 hours, 12 hours, 24 hours, 2 days, 3 days, 5 days, 1 week, two weeks or one month.

In some embodiments, PTZ is administered during a period of at least 1 week, at least 2 weeks, at least 1 month, at least 2 months, at least 3 months, at least 6 months, at least 9 months, at least 1 year, at least 2 years, at least 3 years, at least 4 years, at least 5 years, at least 8 years, or at least 10 years. In some embodiments, PTZ is administered chronically. For example, PTZ can be administered over years of the lifetime of a subject or for the lifetime of the subject.

In some embodiments, the dose of PTZ is administered once daily, twice daily, three times daily, four times daily, or more.

In some embodiments, the PTZ is administered two or three times per day at doses of about 200 mg to 300 mg. In some embodiments, the daily dose of PTZ is about 400 mg to 900 mg.

In some embodiments, PTZ is administered at a once daily dose of about 5 gm, about 4 gm, about 3 gm, about 2 gm, about 1.5 gm, about 1.25 gm, about 1 gm, about 750 mg, about 500 mg, about 250 mg, about 200 mg, about 100 mg, about 50 mg, about 25 mg, about 10 mg, about 5 mg, about 1 mg, about 0.5 mg, about 0.25 mg, or about 0.05 mg.

In some embodiments, the PTZ is administered two or three times per day at doses of about 50 mg to 300 mg, about 100 mg to 200 mg, or about 5 mg to 50 mg. In some embodiments, the PTZ is administered two or three times per day at a dose of about 5 mg. In some embodiments, the PTZ is administered two or three times per day at a dose of about 10 mg. In some embodiments, the PTZ is administered two or three times per day at a dose of about 25 mg. In some embodiments, the PTZ is administered two or three times per day at a dose of about 50 mg. In some embodiments, the PTZ is administered two or three times per day at a dose of about 100 mg. In some embodiments, the PTZ is administered two or three times per day at a dose of about 200 mg. In some embodiments, the daily dose of PTZ is about 100 mg to 800 mg, about 200 mg to 600 mg, or about 300 mg to about 400 mg. In some embodiments, the daily dose of PTZ is about 5 mg to about 100 mg, about 10 mg to 75 mg, or about 25 mg to 50 mg. In some embodiments, the daily dose of PTZ is about 200 mg, about 300 mg, about 400 mg, about 500 mg, about 600 mg, about 700 mg, or about 800 mg. In some embodiments, the daily dose of PTZ is about 5 mg, about 10 mg, about 15 mg, about 20 mg, about 25 mg, about 30 mg, about 50 mg, about 75 mg, about 100 mg, or about 150 mg.

In some embodiments, the PTZ is administered twice daily at a dose of about 100 mg. In some embodiments, the PTZ is administered twice daily at a dose of about 100 mg for a period of at least one week, at least two weeks, or at least 3 weeks. In some embodiments, the daily dose of PTZ is about 200 mg.

In some embodiments, the PTZ is administered twice daily. For example, PTZ can be administered twice daily at a dose from about 25 mg to about 300 mg per each of the two daily administrations. In some embodiments, PTZ is administered twice daily at a dose of about 200 mg per each of the two daily administrations. In some embodiments, the PTZ is administered twice daily at a dose of about 200 mg per at each of the two daily administrations for a period of at least one week, at least two weeks, or at least three weeks. In some embodiments, the daily dose of PTZ is about 600 mg.

In some embodiments, the PTZ is administered three times daily. For example, PTZ can be administered three times a day at a dose from about 25 mg to about 300 mg per each of the three daily administrations. In some embodiments, PTZ is administered three times daily at a dose of about 200 mg per each of the three daily administrations. In some embodiments, the PTZ is administered three times daily at a dose of about 200 mg per at each of the three daily administrations for a period of at least one week, at least two weeks, or at least three weeks. In some embodiments, the daily dose of PTZ is about 600 mg.

In some embodiments, the method comprises the step of administering to the subject a derivative of PTZ, as defined above, at a dose of between 0.005 mg/kg and 20 mg/kg, between 0.01 mg/kg and 10 mg/kg, between 0.001 mg/kg and 0.2 mg/kg, between 0.01 mg/kg and 2 mg/kg, between 0.03 mg/kg and 6 mg/kg, or between 0.05 mg/kg and 0.5 mg/kg.

In some embodiments, the method comprises the step of administering to the subject a derivative of PTZ at a dose of about 20 mg/kg of patient weight, about 10 mg/kg, about 5 mg/kg, about 3 mg/kg, about 1 mg/kg, about 0.3 mg/kg, about 0.1 mg/kg, about 0.05 mg/kg, about 0.025 mg/kg, or about 0.01 mg/kg.

In some embodiments, the method comprises the step of administering to the subject a derivative of PTZ at a daily dose of from 0.1 mg/day to 5 gm/day, from 1 mg/day to 1 g/day, from 3 mg/day to 300 mg/day, from 10 mg/day to 300 mg/day, from 50 mg/day to 300 mg/day, from 100 mg/day to 300 mg/day, or from 150 mg/day to 250 mg/day. In some embodiments, the method comprises the step of administering to the subject a derivative of PTZ at a daily dose of from 100 mg/day to 800 mg/day, from 200 mg/day to 600 mg/day, or from 400 mg/day to 600 mg/day. In some embodiments, the method comprises the step of administering to the subject a derivative of PTZ at a daily dose of about 200 mg/day, about 300 mg/day, about 400 mg/day, about 500 mg/day, about 600 mg/day, about 700 mg/day, or about 800 mg/day.

In various embodiments, the administered dose of PTZ derivative is about 1.5 gm, about 1.25 gm, about 1 gm, about 750 mg, about 500 mg, about 250 mg, about 200 mg, about 100 mg, about 50 mg, about 25 mg, about 10 mg, about 5 mg, about 1 mg, about 0.5 mg, about 0.25 mg, or about 0.05 mg.

In some embodiments, the method comprises the step of administering to the subject a derivative of PTZ at a dose of about 1 mg to 5 gm, about 1 mg to 3 gm, about 1 mg to 2 gm, about 1 mg to 1.5 gm, about 1 mg to 1.25 gm, about 5 mg to 1 gm, about 10 mg to 800 mg, about 25 mg to 600 mg, about 50 mg to 400 mg, or about 100 mg to 200 mg. In some embodiments, the method comprises the step of administering to the subject a derivative of PTZ at a dose of about 1.5 gm, about 1.25 gm, about 1 gm, about 750 mg, about 500 mg, about 250 mg, about 200 mg, about 100 mg, about 50 mg, about 25 mg, or about 10 mg.

In some embodiments, the method comprises the step of administering to the subject PTZ at a dose sufficient to achieve a mean Cmax of about 25 to 25,000 ng/ml, about 50 to 20,000 ng/ml, about 100 to 15,000 ng/ml, about 500 to 10,000 ng/ml, about 1.00 to 8,000 ng/ml, or about 3,000 to 6,000 ng/ml. In some embodiments, the PTZ is administered at a dose sufficient to achieve a mean Cmax of about 300 to 3,000 ng/ml, about 500 to 3,000 ng/ml, about 1,000 to 3,000 ng/ml, or about 2,000 to 3,000 ng/ml.

In some embodiments, the method comprises the step of administering to the subject a derivative of PTZ, as defined above, at a dose sufficient to achieve a mean Cmax of about 25 to 25,000 ng/ml, about 50 to 20,000 ng/ml, about 100 to 15,000 ng/ml, about 500 to 10,000 ng/ml, about 1,000 to 8,000 ng/ml, or about 3,000 to 6,000 ng/ml. In some embodiments, the method comprises the step of administering to the subject a derivative of PTZ, as defined above, at a dose sufficient to achieve a mean Cmax of about 300 to 3,000 ng/ml, about 500 to 3,000 ng/ml, about 1,000 to 3,000 ng/ml, or about 2,000 to 3,000 ng/ml.

In some embodiments, the Cmax is achieved in a subject's brain.

In some embodiments, the PTZ is formulated to achieve a AUC of about 500 ng*hr/mL to 150,000 ng*hr/mL, about 1,000 ng*hr/mL to 100,000 ng*hr/mL, about 5,000 ng*hr/mL to 50,000 ng*hr/mL, or about 10,000 ng*hr/mL to 20,000 ng*hr/mL. In some embodiments, the PTZ is formulated to achieve an AUC of about 1,000 ng*hr/mL to 15,000 ng*hr/mL, about 2,500 ng*hr/mL to 12,500 ng*hr/mL, about 5,000 ng*hr/mL to 10,000 ng*hr/mL, or about 7,500 ng*hr/mL to 12,000 ng*hr/mL.

In some embodiments, the derivative of PTZ is formulated to achieve an AUC of about 500 ng*hr/mL to 150,000 ng*hr/mL, about 1,000 ng*hr/mL to 100,000 ng*hr/mL, about 5,000 ng*hr/mL to 50,000 ng*hr/mL, about 10,000 ng*hr/mL to 20,000 ng*hr/mL. In some embodiments, the derivative of PTZ is formulated to achieve an AUC of about 1,000 ng*hr/mL to 15,000 ng*hr/mL, about 2,500 ng*hr/mL to 12,500 ng*hr/mL, about 5,000 ng*hr/mL to 10,000 ng*hr/mL, or about 7,500 ng*hr/mL to 12,000 ng*hr/mL.

In some embodiments of the methods provided herein, the subject is administered with a composition comprising an active pharmaceutical ingredient (API) and an excipient, wherein the API consists of PTZ, or salt thereof.

In some embodiments, the API consists of a deuterated, fluorinated, or another type of PTZ derivative, or salt thereof.

Administration

The $GABA_A$ chloride channel blocker may be administered to the subject using any convenient means capable of resulting in the desired improvement on sleepiness. Routes of administration include but are not limited to oral, rectal, parenteral, intravenous, intracranial, intraperitoneal, intradermal, transdermal, intrathecal, intranasal, intracheal, intracapillary, subcutaneous, subdermal, topical, intramuscular, rectal, nasal, inhalation, vaginal, injection into the cerebrospinal fluid, injection into the intracavity, or injection directly into the brain. Oral administration can include, for instance, buccal, lingual, or sublingual administration. Transdermal administration can include, for example, topical administration. The compound that can reduce neuronal inhibition may be systemic after administration or may be localized by the use of regional administration, intramural administration, or use of an implant that acts to retain the active dose at the site of implantation. For a brief review of methods for drug delivery see, e.g., Langer 1990 Science 249:1527-1533.

In some embodiments, the PTZ is administered prior to or during the subject's night-time sleep. In some embodiments, the PTZ is administered prior to or during the subject's morning wake-up period.

In some embodiments, the $GABA_A$ chloride channel blocker can cross the blood brain barrier (BBB) to be bioactive in the central nervous system after oral or parenteral administration. In other embodiments, the compound $GABA_A$ chloride channel blocker cannot cross the BBB. In such embodiments, one strategy for drug delivery through the BBB entails disruption of the BBB, either by osmotic means such as mannitol or leukotrienes, or biochemically by the use of vasoactive substances such as bradykinin. The potential for using BBB opening to target specific agents is also an option. A BBB disrupting agent can be co-administered with the compound that can reduce neuronal inhibition when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to the therapeutic or imaging compounds for use in the invention to facilitate transport across the epithelial wall of the blood vessel. Alternatively, drug delivery behind the BBB can be by intrathecal delivery of therapeutics or imaging agents directly to the cranium, as through an Ommaya reservoir (Balis et al. 1989 Am J. Pediatr. Hematol. Oncol. 11:74-6).

Assessing treatment efficacy can be evaluated using any test or protocol known in the art. In some embodiments, the subject having hypersomnia is assessed according to the Stanford Sleepiness Scale (SSS), the Epworth Sleepiness Scale (ESS). In some embodiments, the subject is assessed using the multiple sleep latency (MSL) test or objective psychomotor vigilance (PVT) tasks. In some embodiments, the subject having hypersomnia is assessed according to the maintenance of wakefulness test (MWT). In some embodiments, the subject is assessed using self-reported mood scores or self-reported sleepiness scores. Such tests can, for instance, be employed to assess sleepiness or wakefulness in a subject administered with a $GABA_A$ chloride channel blocker in accordance with the methods provided herein. In some embodiments, a subject having hypersomnia is assessed for wakefulness or sleepiness both before being treated and after being treated with the $GABA_A$ chloride channel blocker In some embodiments, total scores in the ESS range from 0 to 24. A skilled artisan will recognize that in the ESS scores at the lower end (towards 0) of the scale indicate an improvement in a subject's hypersomnia. In some embodiments, scores of 10 and above indicate significant hypersomnia symptoms in a subject. In some embodiments, changes of 2-3 points in the ESS indicate clinically meaningful improvements in the subject's hypersomnia.

In some embodiments, the subject having hypersomnia improves by at least about 2 points, at least about 3 points, at least about 5 points, at least about, at least about 8 points, at least about 10 points, at least about 12 points, or at least about 16 points on the ESS (e.g., with respect to ESS Total Score). In some embodiments, the subject having hypersomnia improves between about 2 points and 16 points, between about 3 points and 16 points, between about 4 points and 16 points, between about 6 points and 14 points, or between about 8 points and 12 points on the ESS (e.g., with respect to ESS Total Score). In some embodiments, the subject having hypersomnia improves by about 2 points, about 3 points, about 5 points, about 8 points, about 10 points, about 12 points, about 14 points, or about 16 on the ESS (e.g., with respect to ESS Total Score). In some embodiments, the subject having hypersomnia scores about 10 points or more on the ESS before administering PTZ to the subject having hypersomnia and the subject having hypersomnia scores less than about 10 points on the ESS after administering PTZ to the subject having hypersomnia (e.g., with respect to ESS Total Score).

In some embodiments, the subject having hypersomnia is assessed using the Functional Outcomes of Sleep Questionnaire (FOSQ). The FOSQ can, e.g., be administered to the subject by asking the subject to rate the impact of a sleep disorder on a scale on activities within certain categories. In some embodiments, an FOSQ total score is determined. In some embodiments, the FOSQ total score is determined from one or more subscale scores (e.g., 1, 2, 3, 4, 5, 6, 7, 8, or more subscale scores). In some embodiments, the FOSQ subscale scores can include, e.g., a General Productivity Score, a Social Outcome Score, an Activity Level Score, a Vigilance Score, or an Intimate Relationship and Sexual Activity Score. A skilled artisan will recognize that higher FOSQ total or subscale scores indicate an improvement in the subject's hypersomnia. In some embodiments, FOSQ total scores can range from about 5 to 20. In some embodiments, FOSQ subscale scores can range from about 1 to 4.

In some embodiments, the subject having hypersomnia improves by at least about 2 points, at least about 3 points, at least about 5 points, at least about, at least about 8 points, at least about 10 points, at least about 12 points, or at least about 16 points on the FOSQ (e.g., with respect to FOSQ Total Score). In some embodiments, the subject having hypersomnia improves between about 2 points and 16 points, between about 3 points and 16 points, between about 4 points and 16 points, between about 6 points and 14 points, or between about 8 points and 12 points on the FOSQ (e.g., with respect to FOSQ Total Score). In some embodiments, the subject having hypersomnia improves by about 2 points, about 3 points, about 5 points, about 8 points, about 10 points, about 12 points, about 14 points, or about 16 on the FOSQ (e.g., with respect to FOSQ Total Score). In some embodiments, the subject having hypersomnia scores about 10 points or less on the FOSQ before administering PTZ to the subject having hypersomnia and the subject having hypersomnia scores more than about 10 points on the FOSQ after administering PTZ to the subject having hypersomnia (e.g., with respect to FOSQ Total Score). In some embodiments, the subject having hypersomnia improves by about 1.0 or more points or about 2.0 or more points on one or more FOSQ subscales (e.g., General Productivity Score; Social Outcome Score, Activity Level Score, Vigilance Score, Intimate Relationships and Sexual Activity Score). In some embodiments, the subject having hypersomnia improves by about 1.5 point, about 2.0 point, or about 2.5 points in one or more FOSQ subscales. In some embodiments, the subject having hypersomnia improves by between about 1.0 points and 3.0 points, or between about 1.5 points and about 2.0 points on one more FOSQ subscales.

In some embodiments, the subject having hypersomnia is assessed using the Multidimensional Fatigue Inventory (MFI). The MFI is typically a 20-item scale designed to evaluate five dimensions of fatigue. In some embodiments, a total MFI score is calculated. In some embodiments, the MFI can include one or more scales (e.g., 1, 2, 3, 4, 5, 6, 7, 8, or more scales). In some embodiments, the MFI scales can include, e.g., a General Fatigue Scale, a Physical Activity Scale, a Reduced Activity Scale, a Reduced Motivation Scale, or a Mental Fatigue Scale. Generally, in MFI lower scores indicate improvements in the subject's insomnia.

In some embodiments, the subject having hypersomnia improves by at least about 3 points, at least about 4 points, at least about 5 points, at least about 8 points, at least about 10 points, at least about 12 points, or at least about 15 points on an MFI scale (e.g., General Fatigue Scale, Physical Fatigue Scale, Reduced Activity Scale, Reduced Motivation Scale). In some embodiments, the subject having hypersomnia improves by between about 3 points and 15 points, between about 5 points and 12 points, or between about 8 points and 12 points on an MFI scale.

In some embodiments, the subject having hypersomnia is assessed using the Clinical Global Impression of Severity (CGI-S). In some embodiments, in the CGI-S, a score of 1 indicates that the subject is normal and not ill; a score of 2 indicates that the subject is borderline ill; a score of 3 indicates that the subject is mildly ill; a score of 4 indicates that the subject is moderately ill; a score of 5 indicates that the subject is markedly ill; a score of 6 indicates that the subject is severely ill; and a score of 7 indicates that the subject is among the most extremely ill subjects.

In some embodiments, the subject having hypersomnia is assessed using the Clinical Global Impression of Change (CGI-C). In some embodiments, in the CGI-C, a score of 1 indicates that the subject's hypersomnia is very much improved; a score of 2 indicates that the subject's hypersomnia is much improved; a score of 3 indicates that the subject's hypersomnia is minimally improved; a score of 4 indicates that the subject's hypersomnia is unchanged; a score of 5 indicates that the subject's hypersomnia is minimally worse; a score of 6 indicates that the subject's hypersomnia is much worse; a score of 7 indicates that the subject's hypersomnia is very much worse.

In some embodiments, of the methods for treating a hypersomnia, the CGI-S or CGI-C score of the subject having hypersomnia decreases by 1 point or more, 2 points or more, 3 points or more, 4 points or more, or 5 points or more.

In some embodiments, the subject having hypersomnia is assessed using the Beck Depression Inventory (current version, published in 1996, is the BDI-II). In some embodiments, a BDI-II total score is determined. In some embodiments, a BDI-II total score of 0-13 indicates minimal depression; a score of 14-19 indicates mild depression; a score of 20-28 indicates moderate depression; and a score of 29-63 indicates severe depression.

In some embodiments, of the methods for treating a hypersomnia, the BDI-II total score of the subject having hypersomnia decreases by 1 point or more, 5 points or more, 10 points or more, 15 points or more, 20 points or more, or 25 points or more.

In some embodiments, the subject having hypersomnia is assessed using a self-reported fogginess score. It is believed that the fogginess score can be used to evaluate a subject's clarity of thinking, which can reflect the subject's cognitive state. In some embodiments, the subject is asked how foggy the subject feels, e.g., since waking up in the morning or since midday. Scoring in a self-reported fogginess score can, e.g., be scored on a scale from 0 to 3. In some embodiments, a self-reported fogginess score of 0 indicates that the subject does not feel foggy at all; a score of 1 indicates that the subject feels mildly foggy; a score of 2 indicates that the subject feels moderately foggy; and a score of 3 indicates that the subject feels extremely foggy.

In some embodiments, the self-reported fogginess score of the subject having hypersomnia decreases by 1 or more or 2 or more points. In some embodiments, the self-reported fogginess score decreases by between about 0.5 and 2.0 points, or between about 1.0 and 1.5 points. In some embodiments, the self-reported fogginess score decreases by about 1.3 points.

In some embodiments, the subject having hypersomnia is assessed using the maintenance of wakefulness test (MWT). See, e.g., Littner et al., *Sleep* Vol. 28, No. 1, pp. 113-121 (2005). In some embodiments, the MWT comprises determining sleep onset latency (SOL). In some embodiments, is the length of time that it takes a subject to accomplish the transition from full wakefulness to sleep, typically to the lightest of non-REM sleep stages. In some embodiments, a SOL score of about 0 min to 5 min indicates severe sleepiness; a SOL score of about 5 min to 10 min indicates troublesome sleepiness; a SOL score of about 10-15 minutes indicates manageable sleepiness, and a SOL score of about 15-20 minutes indicates a typical ability to maintain wakefulness.

In some embodiments, the SOL score of the subject having hypersomnia increases by at least 1 min, at least 2 min, at least 3 min, at least 4 min, at least 5 min, at least 8 min, at least 10 min, at least 12 min, or at least 15 min. In some embodiments, the SOL score of the subject having hypersomnia increases by about 1 min to 15 min, about 2 min to 12 min, about 3 min to 10 min, or about 4 min to 8 min. In some embodiments, the SOL score of the subject having hypersomnia increases by about 1 min, about 2 min, about 3 min, about 4 min, about 5 min, about 6 min, about 7 min, about 8 min, about 9 min, about 10 min, about 11 min, about 12 min, about 13 min, about 14 min, or about 15 min.

It will be understood that an improvement in a subject's sleepiness or wakefulness can refer to any measurable improvement in an aspect of sleep or wake. In some embodiments, the CSF of the subject having hypersomnia is tested for presence or relative activity (i.e., activity relative to CSF from a subject not having hypersomnia) of an endogenous positive allosteric modulator of the $GABA_A$ receptor.

Assessment of the subject having hypersomnia can be conducted prior to administration of the $GABA_A$ chloride channel blocker, throughout the period of administration of the GABA$_A$ chloride channel blocker or following the administration of the GABA$_A$ chloride channel blocker.

In another aspect provided herein are methods for treating hypersomnia in a subject, wherein the method comprises the step of co-administering to the subject a therapeutically effective amount of PTZ and an additional therapy.

In some embodiments the additional therapy includes GABA$_A$ receptor modulators. In certain embodiments, the additional therapy includes GABA$_A$ receptor antagonists or inverse-agonists. In certain embodiments the additional therapy includes flumazenil, clarithromycin, bicuculline, cicutoxin, thujone, lindane or oenanthotoxin. In certain embodiments, the additional therapy does not include a GABA$_A$ chloride channel blocker.

In some embodiments, the additional therapy comprises co-administering a therapeutically effective amount of one or more additional therapeutic agents. In such embodiments, the term "co-administering" as used herein means that the one or more additional therapeutic agents may be administered together with PTZ as part of a single dosage form (such as a pharmaceutical composition comprising PTZ and the one or more additional therapeutic agents) or as separate, multiple dosage forms. Alternatively, the one or more additional therapeutic agents may be administered prior to, consecutively with, or following the administration of PTZ. The administration of a pharmaceutical composition comprising both PTZ and one or more additional therapeutic agents to a subject does not preclude the separate administration of PTZ or any of the one or more additional therapeutic agent to the subject at another time during a course of treatment. The therapeutically effective amounts of the one or more additional therapeutic agents can be determined by skilled artisan's by well known methods.

In some embodiments of the invention in which one or more additional therapeutic agents are co-administered with PTZ to a subject the therapeutically effective amount of PTZ is less than its therapeutically effective amount when the one or more additional therapeutic agents are not administered. In other embodiments, the therapeutically effective amount of the one or more additional therapeutic agents are less than their therapeutically effective amounts when PTZ is not administered. By administering lower therapeutically effective amounts, undesired side effects associated with high doses of either PTZ or the one or more additional therapeutic agents may be minimized. Other potential advantages (including without limitation enhanced efficacy, improved dosing regimens, and/or reduced drug cost) will be apparent to those of skill in the art.

In yet another aspect, this disclosure provides the use of PTZ alone or together with one or more additional therapeutic agents in the manufacture of a pharmaceutical composition, either as a single composition or as separate dosage forms, for treatment or prevention of a sleep disorder in a subject.

In yet another aspect, the methods of this disclosure further include screening a subject having hypersomnia.

In some embodiments, screening the subject having hypersomnia includes determining the presence or absence of an endogenous positive allosteric GABA$_A$ receptor modulator in the cerebrospinal fluid (CSF) of the subject. In some embodiments, screening the subject having hypersomnia includes determining the levels of an endogenous positive allosteric GABA$_A$ receptor modulator in the CSF of the subject. The endogenous positive allosteric GABA$_A$ receptor modulator can be detected, e.g., in a patch clamp assay. See, e.g., Rye et al., 2012, *Sci. Tansl. Med.* 4, 161ra151 (pages 1-10). In some embodiments, screening the subject having hypersomnia includes comparing the levels of the endogenous positive allosteric modulator of GABA$_A$ receptor function in the CSF of the subject having hypersomnia and a subject not having hypersomnia.

It will be understood that also provided herein are uses of a GABA$_A$ chloride channel blocker in the methods provided throughout the application. In some embodiment, provided herein are uses of a GABA$_A$ chloride channel blocker for the treatment of a hypersomnia, fatigue, tiredness or fogginess in a patient. In some embodiments, the GABA$_A$ chloride channel blocker is PTZ.

Example 1

This prophetic example describes the treatment of hypersomnia by administering PTZ to the human patient having hypersomnia.

The patient is selected for PTZ treatments based on a diagnosis of suspected primary hypersomnia (e.g., idiopathic hypersomnia). The diagnosis is based inter alia on the patient presenting with severe daytime sleepiness despite habitually long sleep (≥70 hours per week). The diagnosis may be confirmed using, e.g., the multiple sleep latency test (MSL) or the objective psychomotor vigilance task (PVT) or by determining presence or absence of an endogenous positive allosteric GABA$_A$ receptor modulator in the cerebrospinal fluid (CSF) of the patient. Patients' sleepiness is scored according to the Epworth Sleepiness Scale (ESS) or Stanford Sleepiness Scale (SSS).

Possible conventional causes of sleepiness are ruled out, e.g., by running toxicology screens for sedative agents or benzodiazepines (BZDs) or metabolic profiling for anemia, iron deficiency or hypothyroidism or other methods.

The patient is asked to keep records of sleep and wake times and sleepiness and mood, upon awakening, mid-awake and pre-sleep on a predetermined scale. The patient is further asked to keep records prior to, during and following the PTZ treatment regimen.

PTZ is administered to the patient at least once a day for at least five days at doses of about 25 mg to 600 mg.

The hypersomnia patient's sleepiness is assessed before, during and after completion of the course of PTZ treatments.

Example 2

This example describes the treatment of hypersomnia by administering PTZ to a human patient having hypersomnia.

The patient was selected for PTZ treatments based on a clinical diagnosis of primary hypersomnia and the presence of an elevated level of an endogenous positive GABA$_A$ receptor allosteric modulator in the cerebrospinal fluid (CSF) of the subject relative to the CSF of a subject not having hypersomnia. The patient's sleepiness was scored according to the Epworth Sleepiness Scale (ESS), the Functional Outcomes of Sleep Questionnaire (FOSQ) Total Score, and the Multidimensional Fatigue Inventory (MFI). Additional clinical parameters recorded during the course of PTZ treatment included the Clinical Global Impression of Severity (CGI-S), the Clinical Global Impression of Change (CGI-C), the Beck Depression Inventory (BDI-II) Total Score and the patient's reported feelings of fogginess.

PTZ was orally administered to the patient twice daily at doses of 100 mg in liquid form in a TANG™ brand juice.

The results of PTZ treatment in the patient are summarized in Table 1.

TABLE 1

Clinical parameters observed in a patient diagnosed
with primary hypersomnia and treated with PTZ

| Clinical Parameter | Before Treatment | After 1 week on PTZ (100 mg, twice daily) |
|---|---|---|
| Epworth Sleepiness Scale (ESS) Total Score | 19 | 13 |
| Functional Outcomes of Sleep Questionnaire (FOSQ) Total Score | 6.5 | 14.5 |
| General Productivity Score | 1.4 | 3.3 |
| Social Outcome Score | 1.0 | 3.0 |
| Activity Level Score | 1.4 | 2.9 |
| Vigilance Score | 1.4 | 3.1 |
| Intimate Relationships and Sexual Activity Score | 1.0 | 2.0 |
| Multidimensional Fatigue Inventory (MFI) | | |
| General Fatigue Scale | 17 | 18 |
| Physical Fatigue Scale | 18 | 14 |
| Reduced Activity Scale | 20 | 16 |
| Reduced Motivation Scale | 14 | 9 |
| Mental Fatigue Scale | 19 | 7 |
| Clinical Global Impression of Severity (CGI-S) | 6 | 5 |
| Clinical Global Impression of Change (CGI-C) | 4 | 3 |
| Beck Depression Inventory (BDI-II) Total Score | 9 | 8 |
| How foggy have you felt since waking up this morning?** | 2.4 | 1.1 |
| How foggy have you felt since midday?** | 2.0 | 0.1 |

**Scores represent average of daily scores over one week

The results shown in Table 1 demonstrate that the patient diagnosed with primary hypersomnia showed meaningful improvements in several clinical parameters after one week of PTZ treatment. For example, the ESS Total Score decreased by 6 points, the FOSQ Total Score increased by 8 points, and several MFI scale scores improved, including on the Physical Fatigue Scale, the Reduced Activity Scale, the Reduced Motivation Scale, and the Mental Fatigue Scale. In addition, the patient improved with respect to CGI-S, CGI-C, and BDI-II, and with respect to the patient's subjective feelings of fogginess.

Example 3

This example describes the treatment of hypersomnia by administering PTZ to two human patients having hypersomnia who were treated with flumazenil (Patient 1) or clarithromycin (Patient 2) prior to the administration of PTZ.

Patient 1 in this Example is the same patient as the patient described in Example 2 and the data shown in Table 2 below builds on the data shown in Table 1.

The patients were selected for PTZ treatments and evaluated as described in Example 2. PTZ was orally administered in liquid form in a TANG™ brand juice.

The patients were first evaluated while receiving flumazenil (Patient 1) or clarithromycin (Patient 2). The patients were then taken off flumazenil or clarithromycin and did not receive any treatment during a 1 week "wash-out" period. A second evaluation of the two patients was performed at the end of the wash-out period. PTZ was then administered to Patient 1 for two weeks. During the first week, PTZ was administered to Patient 1 twice daily at doses of 100 mg, and during the second week PTZ was administered to Patient 1 at doses of 200 mg. PTZ was administered to Patient 2 for one week twice daily at doses of 100 mg. The patients were evaluated at the end of the first week (Patients 1 and 2) and at the end of the second week (Patient 1).

The results of PTZ treatments in the patients are summarized in Table 2 (Patient 1) and Table 3 (Patient 2).

TABLE 2

Clinical parameters observed in a patient diagnosed with primary hypersomnia
who was treated with flumazenil prior to PTZ administration.

| Clinical Parameter | Before PTZ Treatment - On Flumazenil | One week after Flumazenil wash-out | After 1 week on PTZ (100 mg, twice daily) | After 2 weeks on PTZ (200 mg, twice daily in 2nd week) |
|---|---|---|---|---|
| Epworth Sleepiness Scale (ESS) Total Score | 12 | 19 | 13 | 9 |
| Functional Outcomes of Sleep Questionnaire (FOSQ) Total Score | 10 | 6.5 | 14.5 | 17.0 |
| General Productivity Score | 2.4 | 1.4 | 3.3 | 3.7 |
| Social Outcome Score | 3.0 | 1.0 | 3.0 | 3.5 |
| Activity Level Score | 1.4 | 1.4 | 2.9 | 2.9 |
| Vigilance Score | 2.3 | 1.4 | 3.1 | 3.7 |
| Intimate Relationships and Sexual Activity Score | 1.0 | 1.0 | 2.0 | 3.0 |
| Multidimensional Fatigue Inventory (MFI) | | | | |
| General Fatigue Scale | 19 | 17 | 18 | 15 |
| Physical Fatigue Scale | 19 | 18 | 14 | 14 |
| Reduced Activity Scale | 19 | 20 | 16 | 16 |
| Reduced Motivation Scale | 12 | 14 | 9 | 11 |
| Mental Fatigue Scale | 16 | 19 | 7 | 8 |
| Clinical Global Impression of Severity (CGI-S) | 6 | 6 | 5 | 4 |
| Clinical Global Impression | Not | 4 | 3 | 2 |

TABLE 2-continued

Clinical parameters observed in a patient diagnosed with primary hypersomnia who was treated with flumazenil prior to PTZ administration.

| Clinical Parameter | Before PTZ Treatment - On Flumazenil | One week after Flumazenil wash-out | After 1 week on PTZ (100 mg, twice daily) | After 2 weeks on PTZ (200 mg, twice daily in 2$^{nd}$ week) |
|---|---|---|---|---|
| of Change (CGI-C) | analyzed | | | |
| Beck Depression Inventory (BDI-II) Total Score | 16 | 9 | 8 | 5 |
| How foggy have you felt since waking up this morning?** | Not analyzed | 2.4 | 1.1 | 1.0 |
| How foggy have you felt since midday?** | Not analyzed | 2.0 | 0.1 | 0.7 |

**Scores represent average of daily scores over one week

TABLE 3

Clinical parameters observed in a patient diagnosed with primary hypersomnia who was treated with clarithromycin prior to PTZ administration.

| Clinical Parameter | Before PTZ Treatment - On Clarithromycin | One week after Clarithromycin wash-out | After 1 week on PTZ (100 mg, twice daily) |
|---|---|---|---|
| Epworth Sleepiness Scale (ESS) Total Score | 8 | 10 | 8 |
| Functional Outcomes of Sleep Questionnaire (FOSQ) Total Score | 15 | 14.5 | 16.5 |
| General Productivity Score | 3.4 | 3.1 | 3.4 |
| Social Outcome Score | 3.0 | 3.0 | 3.0 |
| Activity Level Score | 2.3 | 2.4 | 3.4 |
| Vigilance Score | 2.1 | 1.9 | 2.9 |
| Intimate Relationships and Sexual Activity Score | 4.0 | 4.0 | 4.0 |
| Multidimensional Fatigue Inventory (MFI) | | | |
| General Fatigue Scale | 17 | 16 | 13 |
| Physical Fatigue Scale | 13 | 11 | 7 |
| Reduced Activity Scale | 9 | 10 | 6 |
| Reduced Motivation Scale | 13 | 11 | 7 |
| Mental Fatigue Scale | 9 | 11 | 6 |
| Clinical Global Impression of Severity (CGI-S) | 4 | 5 | 3 |
| Clinical Global Impression of Change (CGI-C) | Not analyzed | 5 | 2 |
| Beck Depression Inventory (BDI-II) Total Score | 0 | 0 | 0 |
| How foggy have you felt since waking up this morning?** | Not analyzed | 1.6 | 2.1 |
| How foggy have you felt since midday?** | Not analyzed | 1.2 | 1.2 |

**Scores represent average of daily scores over one week

The results shown in Tables 1 and 2 demonstrate the superior efficacy of PTZ relative to flumazenil and clarithromycin in the treatment of hypersomnia in human patients diagnosed with primary hypersomnia. For example, in Patient 1, the ESS, FOSQ, CGI-S, CGI-C and BDI-II scores were all found to be much more improved after only one week of PTZ administration (100 mg, twice daily) compared to when Patient 1 was treated with flumazenil. Additional improvements were observed in the ESS, FOSQ, CGI-S, CGI-C and BDI-II scores of Patient 1 after an additional week of PTZ administration (200 mg, twice daily). Similar trends were observed in Patient 2 after 1 week of treatment (100 mg, twice daily). In Patient 2, the FOSQ, MFI and CGI-S scores were found to be more improved after one week of PTZ administration compared to when Patient 2 was treated with clarithromycin.

The examples set forth herein are provided to give those of ordinary skill in the art a complete disclosure and description of how to make and use the embodiments, and are not intended to limit the scope of the disclosure. Modifications of the above-described modes for carrying out the disclosure that are obvious to persons of skill in the area intended to be within the scope of the following claims.

All publications, patents, and patent applications cited in this specification are incorporated herein by reference as if each such publication, patent, or patent application were specifically and individually indicated to be incorporated herein by reference.

What is claimed is:

1. A method for treating idiopathic hypersomnia in a subject comprising administering pentylenetetrazol (PTZ) to the subject having idiopathic hypersomnia, wherein the administering is effective to treat the idiopathic hypersomnia.

2. The method of claim 1, wherein the PTZ is administered at least once daily for at least five consecutive days.

3. The method of claim 1, wherein the PTZ antagonist is administered once a day, twice a day, three times a day or four times a day.

4. The method of claim 1, wherein the PTZ is administered at a dose of about 1 mg to 1,500 mg.

5. The method of claim 1, wherein the PTZ is administered at a dose of about 5 mg to 1,000 mg.

6. The method of claim 1, wherein the PTZ is administered at a dose of about 10 mg to 800 mg.

7. The method of claim 1, wherein the PTZ is administered at a dose of about 25 mg to 600 mg.

8. The method of claim 1, wherein the PTZ is administered at a dose sufficient to achieve a mean Cmax of about 25 to 25,000 ng/ml.

9. The method of claim 1, wherein the PTZ is administered at a dose sufficient to achieve a mean Cmax of about 50 to 20,000 ng/ml.

10. The method of claim 1, wherein the PTZ is administered at a dose sufficient to achieve a mean Cmax of about 100 to 15,000 ng/ml.

11. The method of claim 1, wherein the PTZ is administered at a dose sufficient to achieve a mean Cmax of about 500 to 10,000 ng/ml.

12. The method of claim 1, wherein the PTZ is administered at a dose sufficient to achieve a mean Cmax of about 1,000 to 8,000 ng/ml.

13. The method of claim 1, wherein the PTZ is administered at a dose sufficient to achieve a mean Cmax of about 3,000 to 6,000 ng/ml.

14. The method of claim 1, wherein the PTZ is administered prior to or during the subject's night-time sleep.

15. The method of claim 1, wherein the PTZ is administered prior to or during the subject's morning wake-up period.

16. The method of claim 1, wherein the Cmax is achieved in the brain.

17. The method of claim 1, wherein the PTZ is administered in an oral formulation.

18. The method of claim 1, wherein the PTZ is administered in a delayed release formulation.

19. The method of claim 18, wherein the delayed release formulation delays the peak concentration of PTZ in brain by 30 minutes to 12 hours from the time of administration.

20. The method of claim 18, wherein the delayed release formulation releases PTZ during the subject's night-time sleep or morning wake-up period.

21. The method of claim 1, wherein the PTZ is administered in a sustained release formulation.

22. The method of claim 21, wherein the sustained release formulation maintains a therapeutically effective dose of the PTZ for 30 minutes to 12 hours after administration.

23. The method of claim 1, wherein the PTZ is formulated to achieve an AUC of about 500 ng*hr/mL to 150,000 ng*hr/mL.

24. The method of claim 1, wherein the PTZ is formulated to achieve an AUC of about 1,000 ng*hr/mL to 100,000 ng*hr/mL.

25. The method of claim 1, wherein the PTZ is formulated to achieve an AUC of about 5,000 ng*hr/mL to 50,000 ng*hr/mL.

26. The method of claim 1, wherein the PTZ is formulated to achieve an AUC of about 10,000 ng*hr/mL to 20,000 ng*hr/mL.

27. The method of claim 1, wherein the PTZ is formulated to achieve an AUC of about 1,000 ng*hr/mL to 50,000 ng*hr/mL.

28. The method of claim 1, wherein the subject is human.

29. The method of claim 1, wherein PTZ is administered twice daily at dose of 100 mg for a period of at least one week.

* * * * *